US008211686B2

(12) United States Patent
Djurup et al.

(10) Patent No.: US 8,211,686 B2
(45) Date of Patent: *Jul. 3, 2012

(54) PURIFICATION OF VACCINIA VIRUS- AND RECOMBINANT VACCINIA VIRUS-BASED VACCINES

(75) Inventors: Rene Djurup, Gentofte (DK); Sara Post Hansen, Hoersholm (DK)

(73) Assignee: Bavarian Nordic A/S, Kvistgaard (DK)

(*) Notice: Subject to any disclaimer, the term of this patent is extended or adjusted under 35 U.S.C. 154(b) by 0 days.

This patent is subject to a terminal disclaimer.

(21) Appl. No.: 13/215,258

(22) Filed: Aug. 23, 2011

(65) Prior Publication Data

US 2011/0300181 A1    Dec. 8, 2011

Related U.S. Application Data

(63) Continuation of application No. 12/598,362, filed as application No. PCT/EP2008/003679 on May 7, 2008, now Pat. No. 8,012,738.

(60) Provisional application No. 60/924,413, filed on May 14, 2007.

(51) Int. Cl.
*C12N 7/02* (2006.01)
*A61K 39/285* (2006.01)

(52) U.S. Cl. .................. 435/239; 424/199.1; 424/232.1

(58) Field of Classification Search ......................... None
See application file for complete search history.

(56) References Cited

U.S. PATENT DOCUMENTS

| 6,267,967 | B1  | 7/2001 | Johnston |  |
|---|---|---|---|---|
| 8,003,363 | B2* | 8/2011 | Djurup et al. | 435/239 |
| 8,003,364 | B2* | 8/2011 | Post Hansen et al. | 435/239 |
| 8,012,738 | B2* | 9/2011 | Djurup et al. | 435/239 |
| 2003/0165477 | A1 | 9/2003 | Balloul |  |
| 2007/0071769 | A1 | 3/2007 | Sutter |  |
| 2010/0112001 | A1 | 5/2010 | Djurup |  |
| 2010/0119552 | A1 | 5/2010 | Hansen |  |
| 2010/0129326 | A1 | 5/2010 | Djurup |  |

FOREIGN PATENT DOCUMENTS

WO    WO03/054175 A1    7/2003

OTHER PUBLICATIONS

Baba et al., Sulfated Polysaccharides Are Potent and Selective Inhibitors of Various Enveloped Viruses, Including Herpes Simplex Virus, Cytomegalovirus, Vesicular Stomatitis Virus, and Human Immunodeficiency Virus, Antimicrobial Agents and Chemotherapy 32 (1988) 1742-1745.

Chattopadhyay et al., Polysaccharides from *Gracilaria corticata*: Sulfation, chemical characterization and anti-HSV activities, International Journal of Biological Macromolecules 43 (2008) 346-351.
Enden et al., A model of the dynamics of insect cell infection at lowmultiplicity of infection, Journal of Theoretical Biology 237 (2005) 257-264.
Ho et al., The Oligomeric Structure of Vaccinia Viral Envelope Protein A27L is Essential for Binding to Heparin and Heparan Sulfates on Cell Surfaces: A Structural and Functional Approach Using Site-specific Mutagenesis, J. Mol. Biol. (2005) 349,1060-1071.
Hsaio et al., Cell Surface Proteoglycans Are Necessary for A27L Protein-Mediated Cell Fusion: Identification of the N-Terminal Region of A27L Protein as the Glycosaminoglycan-Binding Domain, Journal of Virology 72 (1998) 8374-8379.
Hsaio et al., Vaccinia Virus Envelope D8L Protein Binds to Cell Surface Chondroitin Sulfate and Mediates the Adsorption of Intracellular Mature Virions to Cells, Journal of Virology 73 (1999) 8750-8761.
Kalbfuss et al., Purification of Cell Culture-Derived Human Influenza a Virus by Size-Exclusion and Anion-Exchange Chromatography, Biotechnology and Bioengineering 96 (2007) 932-944.
Lin et al., Vaccinia Virus Envelope H3L Protein Binds to Cell Surface Heparan Sulfate and is Important for Intracellular Mature Virion Morphogenesis and Virus Infection In Vitro and In Vivo, Journal of Virology 74 (2000) 3353-3365.
Lycke et al., Binding of herpes simplex virus to cellular heparan sulphate, an initial step in the adsorption process, Journal of General Virology (1991) 72, 1131-1137.
Mitsuya et al., Dextran Sulfate Suppression of Viruses in the HIV Family: Inhibition of Virion Binding to CD4+ Cells, Science 240 (1988) 646-649.
O'Keeffe et al., The Affinity Adsorptive Recovery of an Infectious Herpes Simplex Virus Vaccine, Biotechnology and Bioengineering 62 (1999) 537-545.
Opitz et al., Lectin-affinity chromatography for downstream processing of MDCK cell culture derived human influenza A viruses, Vaccine 25 (2007) 939-947.
Opitz et al., Sulfated Membrane Adsorbers for Economic Pseudo-Affinity Capture of Influenza Virus Particles, Biotechnology and Bioengineering 103 (2009) 1144-1154.
Peixoto et al., Towards Purification of Adenoviral Vectors Based on Membrane Technology, Biotechnol. Prog. 2008, 24, 1290-1296.

(Continued)

*Primary Examiner* — Mary E Mosher
(74) *Attorney, Agent, or Firm* — Law Office of Salvatore Arrigo and Scott Lee, LLP

(57) ABSTRACT

The present invention relates to methods for purification of Vaccinia viruses (W) and/or Vaccinia virus (W) particles, which can lead to highly pure and stable virus preparations of predominantly biologically active viruses. The invention encompasses purifying a virus preparation in a sterilized way with high efficiency and desirable yield in terms of purity, biological activity and stability, aspects advantageous for industrial production.

16 Claims, No Drawings

OTHER PUBLICATIONS

Piret et al., In Vitro and In Vivo Evaluations of Sodium Lauryl Sulfate and Dextran Sulfate as Microbicides against Herpes Simplex and Human Immunodeficiency Viruses, Journal of Clinical Microbiology 38 (2000) 110-119.

Resch et al., Protein composition of the vaccinia virus mature virion, Virology 358 (2007) 233-247.

Smith et al., The formation and function of extracellular enveloped vaccinia virus, Journal of General Virology (2002) 83, 2915-2931.

Wu et al., Ion-Exchange Membrane Chromatography Method for Rapid and Efficient Purification of Recombinant Baculovirus and Baculovirus gp64 Protein, Human Gene Therapy (2007) 18:665-672.

Harrer et al., Therapeutic vaccination of HIV-1-infected patients on HAART with a recombinant HIV-1 nef-expressing MVA: safety, immunogenicity and influence on viral load during treatment interruption, Antiviral Therapy 10:285-300 (2005).

Shen et al., Fighting Cancer with Vaccinia Virus: Teaching New Tricks to an Old Dog, Molecular Therapy 11:180-195 (2005).

Chung et al., A27L Protein Mediates Vaccinia Virus Interaction with Cell Surface Heparan Sulfate, Journal of Virology 72:1577-1585 (1998).

Zahn et al., Hepatitis C virus and hepatitis B virus bind to heparin: purification of largely IgG-free virions from infected plasma by heparin chromatography, J. Gen. Virology 86:677-685 (2005).

Broder et al., Recombinant Vaccinia Viruses, Molecular Biotechnology 13:223-245 (1999).

Wolff et al., Capturing of Cell Culture-Derived Modified Vaccinia Ankara Virus by Ion Exchange and Pseudo-Affinity Membrane Adsorbers, Biotechnology and Bioengineering 105: 761-769 (2010) [e-pub Nov. 4, 2009].

O'Neil et al., Virus Harvesting and Affinity-based Liquid Chromatograpy, Bio/Technology vol. 11:173-178 (1993).

\* cited by examiner

PURIFICATION OF VACCINIA VIRUS- AND RECOMBINANT VACCINIA VIRUS-BASED VACCINES

CROSS-REFERENCE TO RELATED APPLICATIONS

This application is a continuation of U.S. application Ser. No. 12/598,362, filed Oct. 30, 2009 now U.S. Pat. No. 8,012, 738, which was the U.S. National Stage of International Application No. PCT/EP2008/003679 filed May 7, 2008, which claims the benefit of U.S. Provisional Application No. 60/924,413, filed May 14, 2007, all of which are incorporated herein by reference.

FIELD OF THE INVENTION

The present invention provides methods for purification of native and recombinant Vaccinia virus and/or Vaccinia virus particles. According to the present invention, the use of this method facilitates purification of a vaccine with high efficiency and desirable yield in terms of purity, biological activity, and stability and is furthermore applicable for an aseptic production process in lab-, pilot-, and industrial-scale.

DESCRIPTION OF RELATED ART

Traditionally in medicine, a vector is a living organism that does not cause disease itself, but which spreads infection by "carrying" pathogens (agents that cause disease) from one host to another. A vaccine vector is a weakened or killed version of a virus or bacterium that carries an inserted antigen (coding for a protein recognized by the body as foreign) from a disease-causing agent to the subject being vaccinated. A vaccine vector delivers the antigen in a natural way into the body and stimulates the immune system into acting against a "safe infection." The immune system is led into generating an immune response against the antigen that protects the vaccinated subject against future "risky infections."

In vaccine development, a recombinant modified virus can be used as the vehicle or vaccine vector for delivering genetic material to a cell. Once in the cell, genetic information is transcribed and translated into proteins, including the inserted antigen targeted against a specific disease. Treatment is successful if the antigen delivered by the vector into the cell produces a protein, which induces the body's immune response against the antigen and thereby protects against the disease.

A viral vector can be based on an attenuated virus, which cannot replicate in the host but is able to introduce and express a foreign gene in the infected cell. The virus or the recombinant virus is thereby able to make a protein and display it to the immune system of the host. Some key features of viral vectors are that they can elicit a strong humoral (B-cell) and cell-mediated (T-cell) immune response.

Viral vectors are commonly used by researchers to develop vaccines for the prevention and treatment of infectious diseases and cancer, and of these, poxviruses (including canary pox, vaccinia, and fowl pox) are the most common vector vaccine candidates.

Pox viruses are a preferred choice for transfer of genetic material into new hosts due to the relatively large size of the viral genome (appr. 150/200 kb) and because of their ability to replicate in the infected cell's cytoplasm instead of the nucleus, thereby minimizing the risk of integrating genetic material into the genome of the host cell. Of the pox viruses, the vaccinia and variola species are the two best known. The virions of pox viruses are large as compared to most other animal viruses (for more details see Fields et al., eds., Virology, 3rd Edition, Volume 2, Chapter 83, pages 2637 ff).

Variola virus is the cause of smallpox. In contrast to variola virus, vaccinia virus does not normally cause systemic disease in immune-competent individuals and it has therefore been used as a live vaccine to immunize against smallpox. Successful worldwide vaccination with Vaccinia virus culminated in the eradication of smallpox as a natural disease in the 1980s (The global eradication of smallpox. Final report of the global commission for the certification of smallpox eradication; History of Public Health, No. 4, Geneva: World Health Organization, 1980). Since then, vaccination has been discontinued for many years, except for people at high risk of poxvirus infections (for example, laboratory workers). However, there is an increasing fear that, for example, variola causing smallpox may be used as a bio-terror weapon. Furthermore, there is a risk that other poxviruses such as cowpox, camelpox, and monkeypox may potentially mutate, through selection mechanisms, and obtain similar phenotypes as variola. Several governments are therefore building up stockpiles of Vaccinia-based vaccines to be used either pre-exposure (before encounter with variola virus) or post-exposure (after encounter with variola virus) of a presumed or actual smallpox attack.

Vaccinia virus is highly immune-stimulating and provokes strong B-(humoral) and T-cell mediated immunity to both its own gene products and to any foreign gene product resulting from genes inserted in the Vaccinia genome. Vaccinia virus is therefore seen as an ideal vector for vaccines against smallpox and other infectious diseases and cancer in the form of recombinant vaccines. Most of the recombinant Vaccinia viruses described in the literature are based on the fully replication competent Western Reserve strain of Vaccinia virus. It is known that this strain has a high neurovirulence and is thus poorly suited for use in humans and animals (Morita et al. 1987, Vaccine 5, 65-70).

In contrast, the Modified Vaccinia virus Ankara (MVA) is known to be exceptionally safe. MVA has been generated by long-term serial passages of the Chorioallantois Vaccinia Ankara (CVA) strain of Vaccinia virus on chicken embryo fibroblast (CEF) cells (for review see Mayr, A. et al. 1975, Infection 3, 6-14; Swiss Patent No. 568,392). Examples of MVA virus strains deposited in compliance with the requirements of the Budapest Treaty are strains MVA 572, MVA 575, and MVA-BN deposited at the European Collection of Animal Cell Cultures (ECACC), Salisbury (UK) with the deposition numbers ECACC V94012707, ECACC V00120707 and ECACC V00083008, respectively, and described in U.S. Pat. Nos. 7,094,412 and 7,189,536.

MVA is distinguished by its great attenuation profile compared to its precursor CVA. It has diminished virulence or infectiousness, while maintaining good immunogenicity. The MVA virus has been analyzed to determine alterations in the genome relative to the wild type CVA strain. Six major deletions of genomic DNA (deletion I, II, III, IV, V, and VI) totaling 31,000 base pairs have been identified (Meyer, H. et al. 1991, J. Gen. Virol. 72, 1031-1038). The resulting MVA virus became severely host-cell restricted to avian cells. The excellent properties of the MVA strain have been demonstrated in extensive clinical trials (Mayr, A. et al. 1978, Zbl. Bakt. Hyg. I, Abt. Org. B 167, 375-390; Stickl, H. et al. 1974, Dtsch. med. Wschr. 99, 2386-2392), where MVA 571 has been used as a priming vaccine at a low dose prior to the administration of conventional smallpox vaccine in a two-step program and was without any significant adverse events (SAES) in more than 120,000 primary vaccinees in Germany (Stickl, H et al. 1974, Dtsch. med. Wschr. 99, 2386-2392; Mayr et al. 1978, Zbl. Bakt. Hyg. I, Abt. Org. B 167, 375-390).

MVA-BN® is a virus used in the manufacturing of a stand-alone third generation smallpox vaccine. MVA-BN® was developed by further passages from MVA strain 571/572. To date, more than 1500 subjects including subjects with atopic dermatitis (AD) and HIV infection have been vaccinated in clinical trials with MVA-BN® based vaccines.

The renewed interest in smallpox vaccine-campaigns with Vaccinia-based vaccines has initiated an increased global demand for large-scale smallpox vaccine production. Furthermore, the use of Vaccinia virus as a tool for preparation of recombinant vaccines has additionally created significant industrial interest in methods for manufacturing (growth and purification) of native Vaccinia viruses and recombinant-modified Vaccinia viruses.

Viruses used in the manufacturing of vaccines or for diagnostic purposes can be purified in several ways depending on the type of virus. Traditionally, purification of pox viruses including Vaccinia viruses and recombinant-modified Vaccinia viruses has been carried out based on methods separating molecules by means of their size differences. To enhance removal of host cell contaminants (e.g. DNA and proteins), in particular DNA, the primary purification by means of size separation has been supplemented by secondary methods such as enzymatic digestion of DNA (e.g. Benzonase treatment). Most commonly, the primary purification of Vaccinia viruses and recombinant-modified Vaccinia viruses has been performed by sucrose cushion or sucrose gradient centrifugation at various sucrose concentrations. Recently, ultrafiltration has also been applied either alone or in combination with sucrose cushion or sucrose gradient purification.

Vaccinia Viruses-based vaccines have in general been manufactured in primary CEF (Chicken Embryo Fibroblasts) cultures. Vaccines manufactured in primary CEF cultures are generally considered safe as regards residual contaminants. First, it is scientifically unlikely that primary cell cultures from healthy chicken embryos should contain any harmful contaminants (proteins, DNA). Second, millions of people have been vaccinated with vaccines manufactured on CEF cultures without any adverse effects resulting from the contaminants (CEF proteins and CEF DNA). There is, therefore, no regulatory requirement for the level of host cell contaminants in vaccines manufactured in primary CEF cultures, but for each vaccine the manufacturer must document its safety. The regulatory concern for vaccines manufactured in primary CEF cultures relates to the risk of adventitious agents (microorganisms (including bacteria, fungi, mycoplasma/spiroplasma, mycobacteria, rickettsia, viruses, protozoa, parasites, TSE agent) that are inadvertently introduced into the production of a biological product).

In the current methods for purification of Vaccinia viruses, manufactured in primary CEF culture the level of CEF protein may be up to 1 mg/dose and the CEF DNA level may exceed 10 µg/dose of $1 \times 10^8$ as measured by the TCID50. These levels are considered acceptable from a safety and regulatory perspective as long as the individual vaccine manufacturer demonstrates that the levels to be found in the Final Drug Product (FDP) are safe at the intended human indications. Due to the risk of presence of adventitious agents in vaccines manufactured in primary cell cultures and the associated need for extensive, expensive biosafety testing of each vaccine batch manufactured, there is a strong stimulus for the vaccine industry to change to continuous cell lines.

Once a continuous cell line has been characterized the need for testing for adventitious agents of the production batches is minimal.

However, switch from primary to continuous cell culture for production of Vaccinia and Vaccinia recombinant vaccines is expected to impose stricter safety and regulatory requirements. In fact, the regulatory authorities have proposed new requirements for levels of DNA contaminants in vaccines manufactured using continuous cell lines (See Draft FDA guideline), which may be as low as 10 ng host-cell DNA/dose. To achieve such low level of host cell contaminants, new and improved methods for purification are needed.

It appears that vaccinia virions are able to bind to heparin through the surface protein A27L (Chung et al. 1998, J. Virol. 72, 1577-1585). It has further been suggested that affinity chromatography (Zahn, A and Allain, J.-P. 2005, J. Gen. Virol. 86, 677-685) may be used as basis for purification of certain virus preparations.

For efficient purification of vaccinia virus and recombinant vaccinia virus-based vaccines, some significant challenges need to be overcome.

1. Vaccinia virions are far too large to be effectively loaded onto commercially available heparin columns, e.g., the Hi-Trap heparin column from Amersham Biosciences used by others (Zahn, A and Allain, J.-P. 2005, J. Gen. Virol. 86, 677-685) for lab-scale purification of Hepatitis C and B viruses. The Vaccinia virion volume is approximately 125 times larger than Hepatitis virion. (The diameter of the Vaccinia virus is, thus, appr. 250 nm as compared with the hepatitis C and B virions diameter being appr. 50 nm). Thus, available matrices as, e.g., used in the column-based approach may not allow for adequate entrance of virions into the matrix, loading of sufficient amounts of virus particles or sufficiently rapid flow through the column to meet the needs for industrial scale purification. Zahn and Allain worked with virus load up to $1 \times 10^6$ in up to 1.0 ml volume. For pilot-scale purification to achieve sufficient material for early clinical trials virus loading capacity higher than $1 \times 10^{11}$, preferably up $1 \times 10^{13}$, in volumes higher than 5 L, preferably up to 50 L, is needed. For industrial purification of Vaccinia virus loading capacity higher than $1 \times 10^{13}$, preferably higher than $1 \times 10^{14}$ in volumes higher than 300 L, preferably higher than 600 L, is needed.

2. The large size of the Vaccinia virus may prevent effective steric access between the specific surface proteins of the virions and the ligand immobilized to the matrix. Currently described lab-scale methods of use for purification of small virus particles may therefore not be industrially applicable to purification of Vaccinia virus.

3. Due to the high number of functional surface molecules interacting with the ligand used for binding of the Vaccinia virus particles, elution of bound Vaccinia virus may require more harsh and therefore potentially denaturing conditions to elute and recover the Vaccinia virus particles in a biologically effective form in high yields. The matrix, the ligand design, the method of ligand immobilization, and the ligand density may therefore require careful design to mediate an effective binding of the Vaccinia virus and to permit an effective elution of biologically active Vaccinia virus particles.

4. To achieve a bio-specific purification of Vaccinia virus particles with high biological activity there is a need in the art for development of industrially usable ligands identical to or very similar to the presumed native ligand for Vaccinia target cell entry. Thus, use of a ligand displaying highly specific and highly effective binding to the Vaccinia virus would be advantageous as it would improve purification by its ability to specifically sort out biologically active Vaccinia virus particles thereby increasing the purity, viability, and functionality of the purified Vaccinia virus.

5. Vaccinia virions are too large to be sterile filtered. The method used in this invention has therefore been developed by to be applicable for an aseptic industrial-scale manufacturing process in a way ensuring full compliance with regulatory requirements regarding sterility of vaccines. In line with the above and for the purpose of this invention, the column substituted with the ligand should be applicable for sterilization-in-place or should be available as a pre-sterilized unit.

DESCRIPTION OF THE INVENTION

In particular, the present invention is directed to a method for the purification of biologically active Vaccinia virus comprising:
a) loading a solid-phase matrix, to which a ligand is attached, with a Vaccinia virus contained in a liquid-phase culture;
b) washing the matrix, and
c) eluting the virus.

The ligand is a substance that, on the one hand, can be attached to the solid-phase matrix, e.g., by binding or coupling thereto and that, on the other hand, is able to form a reversible complex with the Vaccinia virus. Thus, by interacting with the virus, the virus is reversibly retained. The ligand can be a biological molecule as, for example, a peptide and/or a lectin and/or an antibody and/or, preferably, a carbohydrate. The ligand may also comprise or consist of sulfate. In a further embodiment, the ligand comprises one or more negatively charged sulfate groups. Furthermore, the ligand can also be a hydrophobic molecule as, for example, an aromatic phenyl group. The ligand can be attached to the matrix directly, e.g., by direct binding, or can be attached to the matrix indirectly though another molecule, e.g. by coupling through a linker or spacer.

The solid-phase matrix can be a gel, bead, well, membrane, column, etc. In a preferred embodiment of the invention, the solid-phase comprises or is a membrane, in particular a cellulose membrane. However, a broad range of other polymers modified with specific groups capable to bind the virus can be used. Preferred are hydrophilic polymers. Examples are cellulose derivatives (cellulose esters and mixtures thereof, cellulose hydrate, cellulose acetate, cellulose nitrate); aggarose and its derivatives; other polysaccachrides like chitin and chitosan; polyolefines (polypropylene); polysulfone; polyethersulfone; polystyrene; aromatic and aliphatic polyamides; polysulfonamides; halogenated polymers (polyvinylchlorid, polyvinylfluorid, polyvinylidenfluorid); polyesters; homo- and copolymers of acrylnitrile.

The method and further embodiments of the invention can overcome the limitations of currently known methods preventing industrial-scale, effective purification of Vaccinia virus particles with high biological activity and purity. The method is superior in terms of yield, process time, purity, recovery of biologically active Vaccinia virus particles and costs to existing pilot-scale methods for purification of Vaccinia virus particles, which are primarily based on sucrose-cushion centrifugation and/or diafiltration or non-specific ion-exchange chromatography. It is also superior in terms of yield, process time, purity, recovery of biologically active Vaccinia virus particles, and costs to the only existing large-scale method for purification of Vaccinia virus particles, which is based on ultrafiltration, enzymatic DNA degradation, and diafiltration.

According to the present invention, Vaccinia virus can be purified under aseptic conditions to obtain a biologically active, stable, and highly pure virus preparation in high yield. The Vaccinia viruses can be native or recombinant.

The present invention provides an improved method for aseptic purification of Vaccinia viruses in lab-, pilot-, and, preferably, in industrial-scale, leading to a biologically active, stable and highly pure virus preparation in high yield.

This invention provides a more time-effective and cost-effective process for purification of Vaccinia viruses and recombinant Vaccinia viruses, Modified Vaccinia virus Ankara (MVA) and recombinant MVA, MVA-BN® and recombinant MVA-BN®, leading to a biologically active, stable and highly pure virus preparation in high yield.

In another embodiment, this invention provides virus preparations produced by the method of the invention.

Use of the eluted Vaccinia virus or recombinant Vaccinia virus, or Modified Vaccinia virus Ankara (MVA) or recombinant MVA or MVA-BN® or recombinant MVA-BN®, all preferably obtained by the method according to the present invention, for the preparation of a pharmaceutical composition, in particular a vaccine, is also an embodiment of the invention. The virus and/or pharmaceutical preparation is preferably used for the treatment and/or the prevention of cancer and/or of an infectious disease.

A method for inducing an immune response or for the vaccination of an animal, specifically of a mammal, including a human, in need thereof, characterized by the administration of a Vaccinia virus or recombinant Vaccinia virus, or Modified Vaccinia virus Ankara (MVA) or recombinant MVA or MVA-BN® or recombinant MVA-BN® vaccine prepared by a process comprising a purification step as described above is a further embodiment of the invention.

As used herein, an "attenuated virus" is a strain of a virus whose pathogenicity has been reduced compared to its precursor, for example by serial passaging and/or by plaque purification on certain cell lines, or by other means, so that it has become less virulent because it does not replicate, or exhibits very little replication, but is still capable of initiating and stimulating a strong immune response equal to that of the natural virus or stronger, without producing the specific disease.

According to a further preferred embodiment of the present invention, glucosamine glycan (GAG), in particular heparan sulfate or heparin, or a GAG-like substance is used as ligand.

As used herein, "glycosaminoglycans" (GAGs) are long un-branched polysaccharides consisting of a repeating disaccharide unit. Some GAGs are located on the cell surface where they regulate a variety of biological activities such as developmental processes, blood coagulation, tumor metastasis, and virus infection.

As used herein, "GAG-like agents" are defined as any molecule which is similar to the known GAGs, but can be modified, for example, by the addition of extra sulfate groups (e.g. over-sulfated heparin). "GAG-like ligands" can be synthetic or naturally occurring substances. Additionally, the term "GAG-like ligands" also covers substances mimicking the properties of GAGs as ligands in ligand-solid-phase complexes. One example for a "GAG-like ligand" mimicking GAG, specifically heparin, as ligand is Sulfate attached to Reinforced Cellulose as solid-phase, thus forming Sulfated Reinforced Cellulose (SRC) as ligand-solid-phase complex. The use of SRC complex is also a preferred embodiment of the present invention. Stabilized Reinforced Cellulose membranes can be obtained, for example, from Sartorius AG.

As used herein, "Bulk Drug Substance" refers to the purified virus preparation just prior to the step of formulation, fill and finish into the final vaccine.

As used herein, "Biological activity" is defined as Vaccinia virus virions that are either 1) infectious in at least one cell type, e.g. CEFs, 2) immunogenic in humans, or 3) both infectious and immunogenic. A "biologically active" Vaccinia virus is one that is either infectious in at least one cell type, e.g. CEFs, or immunogenic in humans, or both. In a preferred embodiment, the Vaccinia virus is infectious in CEFs and is immunogenic in humans.

As used herein, "contaminants" cover any unwanted substances which may originate from the host cells used for virus growth (e.g. host cell DNA or protein) or from any additives used during the manufacturing process including upstream (e.g. gentamicin) and downstream (e.g. Benzonase).

As used herein, "continuous cell culture (or immortalized cell culture)" describes cells that have been propagated in culture since the establishment of a primary culture, and they are able to grow and survive beyond the natural limit of senescence. Such surviving cells are considered as immortal. The term immortalized cells were first applied for cancer cells which were able to avoid apoptosis by expressing a telomere—lengthening enzyme. Continuous or immortalized cell lines can be created e.g. by induction of oncogenes or by loss of tumor suppressor genes.

As used herein, "heparan sulfate" is a member of the glycosaminoglycan family of carbohydrates. Heparan sulfate is very closely related in structure to heparin, and they both consist of repeating disaccharide units which are variably sulfated. The most common disaccharide unit in heparan sulfate consists of a glucuronic linked to N-acetyl glucosamine, which typically makes up approx. 50% of the total disaccharide units.

As used herein, "heparin" is a member of the glycosaminoglycan family of carbohydrates. Heparin is very closely related in structure to heparan sulfate, and they both consist of repeating disaccharide units which are variably sulfated. In heparin, the most common disaccharide unit consists of a sulfated iduronic acid linked to a sulfated glucopyranosyl. To differentiate heparin from heparan sulfate, it has been suggested that in order to qualify a GAG as heparin, the content of N-sulfate groups should largely exceed that of N-acetyl groups and the concentration of 0-sulfate groups should exceed those of N-sulfate (Gallagher et al. 1985, Biochem. J. 230: 665-674).

As used herein, "industrial scale" or large-scale for the manufacturing of Vaccinia virus or recombinant Vaccinia virus-based vaccines comprises methods capable of providing a minimum of 50,000 doses of $1.0\times10^8$ virus particles (total minimum $5.0\times10^{12}$ virus particles) per batch (production run). Preferably, more than 100,000 doses of $1.0\times10^8$ virus particles (total minimum $1.0\times10^{13}$ virus particles) per batch (production run) are provided.

As used herein, "lab-scale" comprises virus preparation methods of providing less than 5,000 doses of $1.0\times10^8$ virus particles (total less than $5.0\times10^{11}$ virus particles) per batch (production run).

As used herein, "pilot-scale" comprises virus preparation methods of providing more than 5,000 doses of $1.0\times10^8$ virus particles (total more than $5.0\times10^{11}$ virus particles), but less than 50,000 doses of $1.0\times10^8$ virus particles (total minimum $5.0\times10^{12}$ virus particles) per batch (production run).

As used herein, "Primary cell culture", refers to the stage where the cells have been isolated from the relevant tissue (e.g. from specific pathogen free (SPF) hens eggs), but before the first sub-culture. This means that the cells have not been grown or divided any further from the original origin.

As used herein, "Purity" of the Vaccinia virus preparation or vaccine is investigated in relation to the content of the impurities DNA, protein, Benzonase, and gentamicin. The purity is expressed as specific impurity, which is the amount of each impurity per dose (e.g. ng DNA/dose).

As used herein, "purification" of a Vaccinia virus preparation refers to the removal or measurable reduction in the level of some contaminant in a Vaccinia virus preparation.

As used herein, "Recombinant Vaccinia virus" is a virus, where a piece of foreign genetic material (from e.g. HIV virus) has been inserted into the viral genome. Thereby, both the Vaccinia virus genes and any inserted genes will be expressed during infection of the Vaccinia virus in the host cell.

As used herein, "Stability" means a measure of how the quality of the virus preparation (Bulk Drug Substance (BDS) or Final Drug Product (FDP)) varies with time under the influence of a variety of environmental factors such as temperature, humidity and lights, and establishes a retest period for the BDS or a shelf-life for the FDP at recommended storage conditions (Guidance for industry Q1A (R2).

As used herein, a "Virus preparation" is a suspension containing virus. The suspension could be from any of the following steps in a manufacturing process: after virus growth, after virus harvest, after virus purification (typically the BDS), after formulation, or the final vaccine (FDP).

As used herein "vaccinia virus forms" refer to the three different types of virions produced by infected target cells: Mature virions (MV), wrapped virions (WV), and extra-cellular virions (EV) (Moss, B. 2006, Virology, 344:48-54). The EV form comprises the two forms previously known as cell-associated enveloped virus (CEV), and extra-cellular enveloped virus (EEV) (Smith, G. L. 2002, J. Gen. Virol. 83: 2915-2931).

The MV and EV forms are morphologically different since the EV form contains an additional lipoprotein envelope. Furthermore, these two forms contain different surface proteins (see Table 1), which are involved in the infection of the target cells by interaction with surface molecules on the target cell, such as glycosaminglycans (GAGs) (Carter, G. C. et al. 2005, J. Gen. Virol. 86: 12791290). The invention involves use of the purification of all forms of Vaccinia Virus.

The different forms of Vaccinia virions contain different surface proteins, which are involved in the infection of the target cells by interaction with surface molecules on the target cell, such as glycosaminglycans (GAGs) (Carter, G. C. et al. 2005, J. Gen. Virol. 86: 1279-1290). These surface proteins will as mentioned supra be referred to as receptors. On the MV form, a surface protein named p14 or A27L (the latter term will be used in this application) is involved in the initial attachment of the virions to the target cell. A27L binds to GAG structures on the target cell prior to entry into the cell (Chung C. et al. 1998, J. Virol. 72: 1577-1585), (Hsiao J. C. et al. 1998 J. Virol. 72: 8374-8379), (Vazquez M. et al. 1999, J. Virol. 73: 9098-9109) (Carter G. C. et al. 2005, J. Gen. Virol. 86: 1279-1290). The natural ligand for A27L is presumed to be the GAG known as heparan sulfate (HS). Heparan Sulfate belongs to a group of molecules known as glycosaminglycans (GAGs). GAGs are found ubiquitously on cell surfaces. (Taylor and Drickamer 2006, Introduction to Glycobiology, $2^{nd}$ edition, Oxford University Press). GAGs are negatively charged molecules containing sulfate groups. The A27L protein is located on the surface of the virions and is anchored to the membrane by interaction with the A17L protein (Rodriguez D. et al. 1993, J. Virol. 67: 3435-3440) (Vazquez M. et al. 1998, J. Virol. 72: 10126-10137). Therefore, the interaction between A27L and AI17L can be kept intact during isolation in order to retain full biological activity of the virions. The specific nature of the protein-protein interaction between A17L and A27L has not been fully elucidated, but it has been suggested that a presumed "Leucine-zipper" region in the A27L is involved in the interaction with A17L (Vazquez M. et al. 19981, J. Virol. 72: 10126-10137).

The invention encompasses the use of the affinity interaction between the A27L surface protein on the MV form and glucosaminglycans, in particular Heparan Sulfate, for purification of the MV form of Vaccinia Virus.

The term "ligand", thus, refers both to a receptor on a target cell and to the specific binding structure attached to a solid-phase matrix used for purification of Vaccinia.

The same principle as described above can be applied to interactions between other target cell surface structures and other Vaccinia surface proteins of the MV form participating in the Vaccinia virus' recognition of, attachment to, entry into and/or fusion with the target cell (see Table 1). Other WV and EV surface proteins are summarized in Table 1. The entire A27L protein, or fragments thereof containing the binding region for the GAG ligand can be used as agents to elute Vaccinia viruses-GAG complexes from a solid-phase column of the invention. Fragments can be readily generated by routine molecular techniques and screened for their ability to dissociate Vaccinia viruses-GAG complexes using routine techniques known in the art, such as by measuring eluted, biologically active virus.

The presumed native GAG-ligand for the MV form of Vaccinia is Heparan Sulfate (HS) and can be one of the suitable ligands. The invention also comprises use of "non-native" ligands for purification of Vaccinia virus. Such non-native ligands are compounds with a high degree of structural and/or conformational similarity to native ligands. As an example, Heparin, which is a close analogue to the native ligand for A27L, HS, can be used for affinity-purification of MV form by interaction with the A27L surface protein, see further below. Heparin has been shown to partially inhibit the binding between target cells and Vaccinia virus and can therefore also be used for affinity purification of the MV form of Vaccinia. Other GAG-ligands and GAG-like ligands can also be used.

In one embodiment of the invention, Heparan Sulfate, used for affinity purification of the MV form of Vaccinia, binds A27L on biologically active Vaccinia viruses, but does not bind inactive Vaccinia viruses or Vaccinia virus fragments.

The ligand makes possible the elution of the bound Vaccinia virus under such mild conditions that the Vaccinia virus fully retain their biologically activity. This means that the structure of A27L and the interaction between A27L and A17L can be kept intact.

The binding and elution characteristics for the GAG-ligand substituted matrix depend not only on the individual characteristics of the matrix and ligand, but also on the interplay between the two.

By modifying e.g. the ligand density or by attaching, e.g. binding or coupling of, the ligand to the matrix by "arms" or "spacers" of different length and chemical characteristics (hydrophobicity, hydrophilicity) the binding strength between the target GAG-ligand structure and the A27L surface protein on the Vaccinia virus can be altered, which can be used to e.g. enhance the capture or ease the elution.

To enhance the purification method, the matrix in the form of a chromatography gel or membrane to be used for the purification preferably:

Has a high pore size (to make as many ligands as possible accessible to the Vaccinia virus)

Has a rigid structure to allow for fast flow rates

Is available in a form permitting direct or indirect attachment, e.g. by binding or coupling, of ligands Is applicable for sterilization in place or available as a pre-sterilized unit, e.g. by using radiation.

In one embodiment, the solid phase matrix is a gel or membrane with a pore size of 0.25 µm, preferably of more than 0.25 µm, more preferably of 1.0-3.0 µm demonstrating a linear flow rate under actual purification conditions of 10 cm/min, preferably 20 cm/min. The pore size of the matrix can be 0.25-0.5 µm, 0.5-0.75 µm, 0.75-1.0 µm, 1.0-2.0 µm, 2.0-3.0 µm, or greater than 3.0 µm.

In one embodiment, with the solid phase matrix containing a heparan sulfate as an immobilized ligand, the virus harvest from the upstream virus growth process is loaded in a crude (unpurified) form with a flow rate of 10 cm/min, preferably 20 cm/min at a virus concentration of $10^6$ virions per mL in pilot scale and $10^7$ virions per mL in industrial scale.

In one embodiment, there are three steps in the purification process of the invention, which are common for most affinity chromatography processes:

1) Loading of Vaccinia virus or Vaccinia recombinant virus onto the solid phase;
2) Washing of the solid phase to remove contaminants; and
3) Elution of the Vaccinia virus or recombinant virus to be isolated.

Step 1. Loading of Vaccinia Virus or Recombinant Virus onto a Solid-Phase Matrix Loading to the solid phase with, e.g., Heparane Sulphate or another GAG or GAG-like structure attached as ligand, can be performed by a batch-, column- or membrane approach.

The membrane approach can have some benefits, specifically for large bio-molecules, in particular for large viruses like Vaccinia viruses: For example, large pore sizes and the availability of the ligand on the surface of the membrane allow high binding capacities of even large viral particles. The membrane approach is, thus, a preferred embodiment of the present invention.

In all embodiments mentioned above, the Vaccinia virus or recombinant virus to be isolated is present in a liquid phase. When the Vaccinia virus or recombinant virus gets close to the GAG or GAG-like ligand the Vaccinia virus will bind specifically to or be "captured by" the GAG-ligand, thereby the Vaccinia virus or recombinant Vaccinia virus can be temporarily immobilized on the solid phase, while the contaminants will remain in the liquid phase.

By appropriate selection of the ligand type, ligand density and ligand steric configuration, the binding parameters of Vaccinia virus via A27L surface protein to the column can be altered, thereby providing means for optimization of the purification parameters.

Step 2. Washing of the Solid Phase to Remove Contaminants

When the binding of the biologically active Vaccinia viruses or recombinant viruses to the ligand has proceeded sufficiently, the host cell contaminants (in particular host cell DNA and proteins) that remain in the liquid phase can be removed by washing the solid phase, to which the Vaccinia virus is bound, with an appropriate washing medium.

Step 3. Eluting the Vaccinia Virus or Recombinant Virus by Specific or Non-Specific Agents The biologically active Vaccinia viruses or recombinant viruses can be eluted. The elution of the captured Vaccinia virus can be performed, for example, by:

1) Agents specifically disrupting the specific interaction between, e.g., the GAG-ligand and the A27L surface protein on the Vaccinia virus (to be called specific agents), or by
2) Agents non-specifically disrupting the electrostatic interaction between, e.g., the negatively charged GAG-ligand and the positively charged A27L surface protein (to be called non-specific agents).

According to further embodiments of the present invention, the Vaccinia virus is eluted with GAG or a GAG-like ligand or part thereof, with the GAG-binding domain of A27L or part thereof, and/or with an 0-glycoside-binding cleaving enzyme.

Elution of the virus is, further, preferably performed with sodium chloride, more preferably by an increasing NaCl concentration gradient ranging from 0.15 M to 2.0 M.

Pre-Treatment

Prior to loading on the solid phase, a pre-treatment of the virus suspension can be performed, specifically in order to remove contaminants from the Vaccinia virus in the liquid-phase culture.

Pre-treatment can be one or more of the following steps either alone or in combination:
1) Homogenization of the Host Cells
   Ultrasound treatment
   Freeze/thaw
   Hypo-osmotic lysis
   High-pressure treatment
2) Removal of Cell Debris
   Centrifugation
   Filtration
3) Removal/Reduction of Host Cell DNA
   Benzonase treatment
   Cationic exchange
   Selective precipitation by cationic detergents According to a further embodiment of the invention, the pH value of the viral suspension is decreased just prior to loading in order to improve the binding of the virus particle to the ligand. The pH value of the viral suspension can be decreased from appr. pH 7.0-8.0 to 4.0-6.9, in particular to pH 4.0, 4.2, 4.4, 4.5, 4.6, 4.8, 5.0, 5.2, 5.4, 5.5, 5.6, 5.8, 6.0, 6.2, 6.4, 6.5, 6.6, 6.8, 6.9. Preferably, the pH value is decreased from pH 7.0-8.0 to pH 5.8. Subsequently, just after loading and before elution, the pH value is again increased to pH 7.0-8.0, in particular to pH 7.0, 7.2, 7.4, 7.5, 7.6, 7.8, 8.0, preferably to pH 7.7, in order to improve the stability of the viral particles.

Post-Treatment

Depending on the agent used for elution of the Vaccinia virus or recombinant virus, post-treatment can be performed to enhance the purity of the virus preparation. The post-treatment could be ultra/diafiltration for further removal of impurities and/or specific or non-specific agents used for elution. To obtain an efficient purification of the virus, it is also preferred to combine the purification according to the invention with one or more further purification steps, e.g., by ion-exchange(s). Ion-exchange(s) can, then, also be performed as post-treatment step(s).

In order to prevent aggregation of the purified virus suspension and, thus, to, inter alia, improve the detection of infectious particles, in particular by the TCID50 method, it can also be suitable to increase the pH value after elution of the virus, in particular to a pH value of up to 9 or more, in particular to pH 7.5, 7.6, 7.8, 8.0, 8.2, 8.4, 8.5, 8.6, 8.8, 9.0, 9.2, 9.4, 9.5, 9.6, 9.8, 10.0, 10.2, 10.4, 10.5. Preferably, the pH value is increased from, in particular, pH 7.0, 7.2, 7.4, 7.5, 7.6, 7.8, 8.0, preferably pH 7.7, to pH 9.0.

According to a further embodiment of the present invention, the Vaccinia virus sample contains host-cell DNA in the range of 10-20 µg per dose ($1\times10^8$ TCID$_{50}$-$3.2\times10^8$ TCID$_{50}$), preferably 10 ng, more preferably less than 10 ng host-cell DNA per $10^8$ virus particles after performance of the purification steps according to the invention, i.e., after elution of the virus.

The practice of the invention employs techniques in molecular biology, protein analysis, and microbiology, which are within the skilled practitioner of the art. Such techniques are explained fully in, for example, Ausubel et al. 1995, eds, Current Protocols in Molecular Biology, John Wiley & Sons, New York.

Modifications and variations of this invention will be apparent to those skilled in the art. The specific embodiments described herein are offered by the way of example only, and the invention is not to be construed as limited thereby.

In one embodiment, the invention provides a more time-effective and cost-effective process for purification of Vaccinia viruses and recombinant-modified Vaccinia viruses in higher yield, comprising one or more of the following steps:
a) loading a solid-phase matrix with a liquid-phase virus preparation, wherein the solid-phase matrix comprises a ligand appropriate for interacting with the virus, e.g. by reversibly binding the virus
b) washing of the matrix, and
c) eluting the virus.

Additional aspects and advantages of the invention will be set forth in part in the description which follows, and in part will be obvious from the description, or may be learned by practice of the invention.

In a preferred embodiment, the method comprises the following steps:
a. Loading a column, membrane, filter or similar solid-phase matrix comprising one or more appropriate virus-binding ligands with a liquid-phase virus preparation,
b. Washing of the matrix with an appropriate solvent to remove contaminants, and
c. Eluting the Vaccinia virus with an appropriate solvent to achieve a highly pure, biologically active, stable virus preparation.

In a further preferred embodiment, the method comprises the following steps:
a. Loading a column, membrane, filter or similar solid-phase matrix comprising one or more appropriate glucosamine glycan (GAG) or GAG-like virus-binding ligands with a liquid-phase virus preparation
b. Washing of the matrix with an appropriate solvent to remove contaminants, and
c. Eluting the Vaccinia virus with a solvent resulting in an concentration gradient of a non-specific eluent such as NaCl, H+ or of specific eluent such as a GAG-like compound or and A27L peptide or peptide-fragment to achieve a highly pure, biologically active, stable virus preparation.

In one particularly preferred embodiment, the method is used for the purification of biologically active Vaccinia virus and comprises the following steps:
a. Loading a column, membrane, filter or similar solid-phase matrix substituted with a Heparin (HP) with a Vaccinia virus preparation dissolved in a neutral buffer (pH 6.5 to 8.5, preferably >=pH 7.5) with a physiological salt concentration (approximately 150 mM NaCl),
b. Washing of the matrix with a sufficient amount of the loading buffer to ensure complete elution of all non-binding Vaccinia virus particles and non-binding contaminants, and c. Eluting the Vaccinia virus with an increasing concentration of NaCl, from 0.15 to 2.0 M NaCl, to initially remove contaminants with less affinity than the Vaccinia virus particles and to finally elute the biologically active Vaccinia virus particles.

In another particularly preferred embodiment, the method is used for the purification of biologically active Vaccinia virus and comprises the following steps:
  a. Loading a column, membrane, filter or similar solid-phase matrix substituted with a Heparin (HP) with a Vaccinia virus preparation dissolved in a neutral buffer (pH 6.5 to 8.5, preferably >=pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M
  b. Washing of the matrix with a sufficient amount of the loading buffer e.g. PBS (0.01 M phosphate, 0.15 M NaCl, pH 7.5) to ensure complete elution of all non-binding Vaccinia virus particles and nonbinding contaminants, as measured by the return of the 280 nm absorbance signal to the pre-loading baseline, and
  c. Eluting the Vaccinia virus with an increasing concentration of NaCl in PBS, starting with 0.15 M and ending with 2.0 M NaCl.

In another particularly preferred embodiment, the method is used for the purification of biologically active Vaccinia virus and comprises the following steps:
  a. Loading a column, membrane, filter or similar solid-phase matrix substituted with a Heparin (HP) with a Vaccinia virus preparation dissolved in a neutral buffer (pH 6.5 to 8.5, preferably >=pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M NaCl, pH 8.0, and HEPES-NaCl, e.g. 0.01 to 0.1 M HEPES, 0.15 M NaCl, pH 7.5,
  b. Washing (Wash 1) of the matrix with a sufficient amount of the loading buffer e.g. PBS (0.01 M phosphate, 0.15 M NaCl, pH 7.5) to ensure complete elution of all non-binding Vaccinia virus particles and non-binding contaminants, as measured by the return of the 280 nm absorbance signal to the pre-loading baseline,
  c. Washing (Wash 2) of the matrix with an additional washing buffer e.g. Glycine Buffered Saline (GBS) 0.02 M, 0.15 M NaCl, pH 9.0) to remove loosely bound contaminants, and
  d. Eluting the Vaccinia virus with an increasing concentration of NaCl in GBS 0.02 M pH 9.0, starting with 0.15 M and ending with 2.0 M NaCl.

In another particularly preferred embodiment, the method is used for the purification of biologically active Vaccinia virus and comprises the following steps:
  a. Loading a column, membrane, filter or similar solid-phase matrix substituted with a Heparane Sulphate (HS) with a Vaccinia virus preparation dissolved in a neutral buffer (pH 6.5 to 8.5, preferably >=pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M
  b. Washing of the matrix with a sufficient amount of the loading buffer e.g. to ensure complete elution of all non-binding Vaccinia virus particles and non-binding contaminants, as measured by the return of the 280 nm absorbance signal to the pre-loading baseline, and
  c. Eluting the Vaccinia virus with an increasing concentration of Low Molecular Weight Heparin, 0.01 to 0.5 M, in PBS 0.1 M, NaCl 0.15 M, pH 7.5.

In another particularly preferred embodiment, the method is used for the purification of biologically active Vaccinia virus and comprises the following steps:
  a. Loading a column, membrane, filter or similar solid-phase matrix substituted with a Heparane Sulphate (HS) with a Vaccinia virus preparation dissolved in Phosphate Buffered Saline (PBS), 0.02 M phosphate, 0.15 M NaCl, pH 7.5,
  b. Washing of the matrix with a sufficient amount of the loading buffer e.g. to ensure complete elution of all non-binding Vaccinia virus particles and non-binding contaminants, as measured by the return of the 280 nm absorbance signal to the pre-loading baseline, and
  c. Eluting the Vaccinia virus with an increasing concentration of an HS-derived oligosaccharide. The basic repeating disaccharide unit in HS-derived oligosaccharide is a,(31-$\beta$4-linked sequence of glucosamine and uronic acid. The glucosamine residues are either N-acetylated (GlcNAc) or N-sulphated (GlcNSO3-). Other monosaccharide residues e.g. iduronic acid and substitutions may occur, e.g. 2-0-sulphated iduronic acid. The oligosaccharide consists of 2 to 10 repeating disaccharide units. The oligosaccharide concentration used for elution of the Vaccinia virus particles runs from 0.01 M to 0.5 M in PBS, 0.02 M phosphate, 0.15 M NaCl, pH 7.5.

In another particularly preferred embodiment, the method is used for the purification of biologically active Vaccinia virus and comprises the following steps:
  a. Loading a column, membrane, filter or similar solid-phase matrix substituted with a Heparane Sulphate (HS) with a Vaccinia virus preparation dissolved in Phosphate Buffered Saline (PBS), 0.02 M phosphate, 0.15 M NaCl, pH 7.5,
  b. Washing of the matrix with a sufficient amount of the loading buffer e.g. to ensure complete elution of all non-binding Vaccinia virus particles and non-binding contaminants, as measured by the return of the 280 nm absorbance signal to the pre-loading baseline, and
  c. Eluting the Vaccinia virus with an increasing concentration of an Vaccinia virus particles surface protein or a peptide or peptide-fragment derived hereof. The preferred surface protein is A27L, the preferred peptide is A27L, and the preferred A27L peptide-fragment is fragment containing 4-10 amino acid residues of the A27L peptide sequence responsible for the binding between A27L and the HS. The peptide concentration used for elution of the Vaccinia virus particles runs from 0.01 M to 0.5 M in PBS, 0.02 M phosphate, 0.15 M NaCl, pH 7.5.

In another particularly preferred embodiment, the method is used for the purification of biologically active Vaccinia virus and comprises the following steps:
  a. Loading a column, membrane, filter or similar solid-phase matrix substituted with a Heparane Sulphate (HS) with a Vaccinia virus preparation dissolved in Phosphate Buffered Saline (PBS), 0.02 M phosphate, 0.15 M NaCl, pH 7.5,
  b. Washing of the matrix with a sufficient amount of the loading buffer e.g. to ensure complete elution of all non-binding Vaccinia virus particles and non-binding contaminants, as measured by the return of the 280 nm absorbance signal to the pre-loading baseline, and c. Eluting the Vaccinia virus with an enzyme capable of partially cleaving one or more glycoside linkages between the repeating disaccharide units, inside the repeating disaccharide unit or elsewhere in the HS molecule. Preferred enzymes are Heparin Lyase I, II and III. The elution is performed by saturation of the column with the enzyme solution. After an appropriate digestion time the unbound complex of Vaccinia virus particles and GAG-residues bound to the Vaccinia virus particles is eluted with PBS, 0.02 M phosphate, 0.15 M NaCl, pH 7.5. The Vaccinia virus particle-GAG-residue complex is dissociated with a mild NaCl solution e.g. PBS 0.02 M, 0.15 M NaCl, pH 7.5 and the GAG-residues are removed by diafiltration.

EXAMPLES

Affinity purifications are made applying either column chromatography with e.g. Toyopearls or membrane chromatography using e.g. a membrane (e.g. Sartobind MA 75 (Sartorius)) both of which are substituted with a GAG-ligand (e.g. Heparin or Heparan Sulfate).

The below mentioned examples are all in lab-scale.

Example 1

1) Two ml of a highly concentrated and previously purified Vaccinia virus preparation with approximately $2 \times 10^9$ virus particles per ml were applied to a column with packed with Toyopearl AF-Heparin.
2) The column was washed with PBS 0.01 M, 0.15 M NaCl, pH 7.2. The A280 absorbance signal used for monitoring of Vaccinia virus particle and host cell protein concentrations returned to baseline (the pre-loading value) after 12 minutes. The washing continued for a total of 25 minutes.
3) The bound Vaccinia virus particles were eluted by a NaCl concentration gradient in PBS 0.01 M, pH 7.2. The concentration of NaCl was increased linearly from 0.15 M to 2.0 M. The elution started after approximately a total of 30 minutes (5 minutes after starting the gradient). The major peak was eluted 7 minutes later (at T=37 minutes). The peak contained a high concentration of Vaccinia virus particles as assessed by the Laser Scattering signal used for monitoring of Vaccinia virus particles. The elution was completed after approximately 25 minutes (T=55 minutes).
4) The eluate was analyzed by a Vaccinia Virus specific ELISA showing a virus recovery rate of appr. 70%-90%. Host cell protein was analysed by use of the BCA total protein assay showing appr. 10% of protein in the eluate. Host cell DNA was analysed by a total DNA assay showing an additional removal of DNA of appr. 40% in the wash and flow-through.

Example 2

1) Two ml of a highly concentrated and previously purified Vaccinia virus preparation with approximately $2 \times 10^9$ virus particles per ml was applied to a Sartobind MA75 Heparin membrane.
2) The membrane was washed with PBS 0.01 M, 0.15 M NaCl, pH 7.5. The A280 absorbance signal used for monitoring of Vaccinia virus particle and host cell protein concentrations returned to baseline (the pre-loading value) after 12 minutes. The washing continued for a total of 16 minutes.
3) The bound Vaccinia virus particles were eluted by a NaCl concentration gradient in PBS 0.01 M, pH 7.5. The concentration of NaCl was increased linearly from 0.15 M to 2.0 M. The elution started after approximately a total of 20 minutes (4 minutes after starting the gradient). The major peak was eluted 5 minutes later (at T=25 minutes). The peak contained a high concentration of Vaccinia virus particles as assessed by the Laser Scattering signal used for monitoring of Vaccinia virus particles.
4) The eluate was analyzed by a Vaccinia Virus specific ELISA showing a virus recovery rate of appr. 55%. Host cell protein was analyzed by use of the BCA total protein assay and revealed a protein recovery of appr. 5% in the eluate. Host cell DNA was analyzed by a total DNA assay and revealed appr. 10% DNA in the eluate.

Example 3

1) Two ml of a highly concentrated Vaccinia virus preparation with approximately $2 \times 10^9$ virus particles per ml are applied to a Sartobind MA75 Heparin membrane.
2) The membrane is washed with PBS 0.01 M, 0.15 M NaCl, pH 7.5. The A280 absorbance signal is used for monitoring of Vaccinia virus particle and the host cell protein concentrations until it returns to baseline (the pre-loading value). The washings are continued for a total of 20 minutes.
3) The bound Vaccinia virus particles are eluted by a pH concentration gradient in GBS 0.02 M, 0.15 M NaCl. The initial pH is 8.5, increasing to pH 10.5. The concentration of NaCl is increased linearly from 0.15 M to 2.0 M.
4) The eluate is analyzed by titration for viable (infectious) Vaccinia virus particles by a Tissue Culture cytopatic effect assay (TCID50), for total number of Vaccinia virus particles by a real-time qPCR for Vaccinia DNA, for host cell protein by use of the BCA total protein assay and for host cell DNA by use of a real-time qPCR. The recovery can be >60% and biological activity of the recovered Vaccinia virus can be >75%.

Example 4

1) Two ml of a highly concentrated Vaccinia virus preparation with approximately $2 \times 10^9$ virus particles per ml are applied to a Sartobind MA75 Heparin membrane.
2) The membrane is washed with PBS 0.01 M, 0.15 M NaCl, pH 7.5. The A280 absorbance signal is used for monitoring of Vaccinia virus particle and the host cell protein concentrations until it returns to baseline (the pre-loading value). The washings are continued for a total of 20 minutes.
3) The elution is performed with a concentration gradient of low-molecular weight heparin (LMW-HP) in PBS 0.1 M, 0.15 M NaCl, pH 7.5. The gradient is run from 0.01 to 0.5 M LMW-Heparin.
4) The eluate is analyzed by titration for viable (infectious) Vaccinia virus particles by a Tissue Culture cytopathic effect assay (TCID50), for total number of Vaccinia virus particles by a real-time qPCR for Vaccinia DNA, for host cell protein by use of the BCA total protein assay and for host cell DNA by use of a real-time qPCR. The recovery can be >70% and biological activity of the recovered Vaccinia virus can be >80%.

Example 5

1) Two ml of a highly concentrated Vaccinia virus preparation with approximately $2\times10^9$ virus particles per ml are applied to a Sartobind MA75 Heparin membrane.
2) The membrane is washed with PBS 0.01 M, 0.15 M NaCl, pH 7.5. The A280 absorbance signal is used for monitoring of Vaccinia virus particle and the host cell protein concentrations until it returns to baseline (the preloading value). The washings are continued for a total of 20 minutes.
3) The elution is performed with a concentration of a gradient of A27L peptide (A27LP) in PBS 0.1 M, 0.15 M NaCl, pH 7.5. The gradient is run from 0.01 to 0.5 M A27LP.
4) The eluate is analyzed by titration for viable (infectious) Vaccinia virus particles by a Tissue Culture cytopatic effect assay (TCID50), for total number of Vaccinia virus particles by a real-time qPCR for Vaccinia DNA, for host cell protein by use of the BCA total protein assay and for host cell DNA by use of a real-time qPCR. The recovery can be >70% and biological activity of the recovered Vaccinia virus can be >80%.

Example 6

1) Two ml of a highly concentrated Vaccinia virus preparation with approximately $2\times10^9$ virus particles per ml are applied to a Sartobind MA75 Heparin membrane.
2) The membrane is washed with PBS 0.01 M, 0.15 M NaCl, pH 7.5. The A280 absorbance signal is used for monitoring of Vaccinia virus particle and the host cell protein concentrations until it returns to baseline (the pre-loading value). The washings are continued for a total of 20 minutes.
3) The elution is performed with a glycoside linkage cleaving enzyme Heparin Lyase in PBS 0.1 M, 0.15 M NaCl, pH 7.5. The membrane is saturated with Heparin Lyase by running 2 volumes of Heparin Lyase through the column.
4) After allowing 60 minutes for enzymatic cleavage of the glycoside linkage, the unbound complexes of Vaccinia virus particles and heparin-residues bound to the Vaccinia virus particles are eluted with PBS, 0.02 M phosphate, 0.15 M NaCl, pH 7.5. The Vaccinia virus particle-GAG-residue complex is dissociated with PBS 0.02 M, 0.3 M NaCl, pH 7.5. The Heparin-residues are removed by diafiltration.
5) The eluate is analyzed by titration for viable (infectious) Vaccinia virus particles by a Tissue Culture cytopatic effect assay (TCID50), for total number of Vaccinia virus particles by a real-time qPCR for Vaccinia DNA, for host cell protein by use of the BCA total protein assay and for host cell DNA by use of a real-time qPCR. The recovery can be >70% and biological activity of the recovered Vaccinia virus can be >80%.

Example 7

1) Two ml of a highly concentrated and previously purified Vaccinia virus preparation with approximately $2\times10^9$ virus particles per ml were applied to a Sulfated Reinforced Cellulose membrane.
2) The membrane was washed with PBS 0.01 M, 0.15 M NaCl, pH 7.5. The A280 absorbance signal was used for monitoring of Vaccinia virus particle and the host cell protein concentrations until it returned to baseline (the pre-loading value). The washings were continued for a total of 25 minutes.
3) The bound Vaccinia virus particles were eluted by a NaCl concentration gradient in PBS 0.01 M, pH 7.5. The concentration of NaCl was increased linearly from 0.15 M to 2.0 M. The elution started after approximately a total of 30 minutes (5 minutes after starting the gradient). The major peak was eluted 5 minutes later (at T=35 minutes). The peak contained a high concentration of Vaccinia virus particles as assessed by the Laser Scattering signal used for monitoring of Vaccinia virus particles.
4) The eluate was analyzed by a Vaccinia Virus specific ELISA showing a virus recovery rate of approx 40%. Host-cell protein was analyzed by use of the BCA total protein assay and showed a protein recovery of approx 5% in the eluate. Host-cell DNA was analyzed by a total DNA assay and showed approx 5% DNA in the eluate.

TABLE 1

| VV surface proteins | | |
|---|---|---|
| Surface protein (gene) | VV form | References |
| A2.5L | MV | [1] |
| A9L | MV | [2] |
| A13L | MV | [3] |
| A14L | MV | [4-7] |
| A14.5L | MV | [8] |
| A16L | MV | [9; 10] |
| A17L | MV | [11-13] |
| A21L | MV | [14] |
| A25L | MV | [15] |
| A26L | MV | [15; 16] |
| A27L | MV | [17-22] |
| A28L | MV | [23; 24] |
| A33R | EV | [25-27] |
| A34 R | EV | [28-31] |
| A36R | WV | [32-37] |
| A38L | | [38; 39] |
| A56R | EV | [40-43] |
| B5R | EV | [44-46] |
| D8L | MV | [47] |
| D13L | MV | |
| E1OR | MV | [48] |
| F9L | MV | [49] |
| F12 | WV | [37; 50] |
| F13L | EV | [51-55] |
| G3L | MV | [9] |
| G4L | MV | [56; 57] |
| G9R | MV | [9; 58] |
| H2 R | MV | [59] |
| H3L | MV | [60-62] |
| I2L | MV | [63] |
| I5L | MV | [64] |
| J5L | MV | [9] |
| K2L | WV/EV | [65-68] |
| L1R | MV | [69] |
| L5R | MV | [70] |

LIST OF REFERENCES CITED IN TABLE 1

(1) Senkevich T G, White C L, Weisberg A, Granek J A, Wolfe E J, Koonin E V, Moss B: Expression of the vaccinia virus A2.5L redox protein is required for virion morphogenesis. Virology 2002; 300(2):296-303.
(2) Yeh W W, Moss B, Wolfe E J: The vaccinia virus A9L gene encodes a membrane protein required for an early step in virion morphogenesis. J Virol 2000; 74(20):9701-9711.
(3) Unger B, Traktman P: Vaccinia virus morphogenesis: a13 phosphoprotein is required for assembly of mature virions. J Virol 2004; 78(16):8885-8901.

(4) Traktman P, Liu K, DeMasi J, Rollins R, Jesty S, Unger B: Elucidating the essential role of the A14 phosphoprotein in vaccinia virus morphogenesis: construction and characterization of a tetracycline-inducible recombinant. J Virol 2000; 74(8):3682-3695.

(5) Rodriguez J R, Risco C, Carrascosa J L, Esteban M, Rodriguez D: Vaccinia virus 15-kilodalton (A14L) protein is essential for assembly and attachment of viral crescents to virosomes. J Virol 1998; 72(2):1287-1296.

(6) Mercer J, Traktman P: Investigation of structural and functional motifs within the vaccinia virus A14 phosphoprotein, an essential component of the virion membrane. J Virol 2003; 77(16):8857-8871.

(7) Betakova T, Wolffe E J, Moss B: Regulation of vaccinia virus morphogenesis: phosphorylation of the A14L and A17L membrane proteins and C-terminal truncation of the AI 7L protein are dependent on the F1OL kinase. J Virol 1999; 73(5):3534-3543.

(8) Betakova T, Wolfe E J, Moss B: The vaccinia virus A14.5L gene encodes a hydrophobic 53-amino-acid virion membrane protein that enhances virulence in mice and is conserved among vertebrate poxviruses. J Virol 2000; 74(9): 4085-4092.

(9) Senkevich T G, Ojeda S, Townsley A, Nelson G E, Moss B: Poxvirus multiprotein entry-fusion complex. Proc Natl Acad Sci USA 2005; 102(51):18572-18577.

(10) Ojeda S, Senkevich T G, Moss B: Entry of vaccinia virus and cell-cell fusion require a highly conserved cysteine-rich membrane protein encoded by the AI 6L gene. J Virol 2006; 80(1):51-61.

(11) Betakova T, Wolfe E J, Moss B: Membrane topology of the vaccinia virus A17L envelope protein. Virology 1999; 261(2):347-356.

(12) Rodriguez D, Esteban M, Rodriguez J R: Vaccinia virus A17L gene product is essential for an early step in virion morphogenesis. J Virol 1995; 69(8):4640-4648.

(13) Wolfe E J, Moore D M, Peters P J, Moss B: Vaccinia virus A17L open reading frame encodes an essential component of nascent viral membranes that is required to initiate morphogenesis. J Virol 1996; 70(5):2797-2808.

(14) Townsley A C, Senkevich T G, Moss B: Vaccinia virus A21 virion membrane protein is required for cell entry and fusion. J Virol 2005; 79(15):9458-9469.

(15) Ulaeto D, Grosenbach D, Hruby D E: The vaccinia virus 4c and A-type inclusion proteins are specific markers for the intracellular mature virus particle. J Virol 1996; 70(6): 3372-3377.

(16) McKelvey T A, Andrews S C, Miller S E, Ray C A, Pickup D J: Identification of the orthopoxvirus p4c gene, which encodes a structural protein that directs intracellular mature virus particles into A-type inclusions. J Virol 2002; 76(22):11216-11225.

(17) Ho Y, Hsiao J C, Yang M H, Chung C S, Peng Y C, Lin T H, Chang W, Tzou D L: The oligomeric structure of vaccinia viral envelope protein A27L is essential for binding to heparin and heparan sulfates on cell surfaces: a structural and functional approach using site-specific mutagenesis. J Mol Biol 2005; 349(5):1060-1071.

(18) Vazquez M I, Esteban M: Identification of functional domains in the 14-kilodalton envelope protein (A27L) of vaccinia virus. J Virol 1999; 73(11):9098-9109.

(19) Hsiao J C, Chung C S, Chang W: Cell surface proteoglycans are necessary for A27L protein-mediated cell fusion: identification of the N-terminal region of A27L protein as the glycosaminoglycan-binding domain. J Virol 1998; 72(10):8374-8379.

(20) Chung C S, Hsiao J C, Chang Y S, Chang W: A27L protein mediates vaccinia virus interaction with cell surface heparan sulfate. J Virol 1998; 72(2):1577-1585.

(21) Vazquez M I, Rivas G, Cregut D, Serrano L, Esteban M: The vaccinia virus 14-kilodalton (A27L) fusion protein forms a triple coiled-coil structure and interacts with the 21-kilodalton (A17L) virus membrane protein through a C-terminal alpha-helix. J Virol 1998; 72(12):10126-10137.

(22) Rodriguez D, Rodriguez J R, Esteban M: The vaccinia virus 14-kilodalton fusion protein forms a stable complex with the processed protein encoded by the vaccinia virus AI 7L gene. J Virol 1993; 67(6):3435-3440.

(23) Senkevich T G, Ward B M, Moss B: Vaccinia virus entry into cells is dependent on a virion surface protein encoded by the A28L gene. J Virol 2004; 78(5):2357-2366.

(24) Senkevich T G, Ward B M, Moss B: Vaccinia virus A28L gene encodes an essential protein component of the virion membrane with intramolecular disulfide bonds formed by the viral cytoplasmic redox pathway. J Virol 2004; 78(5): 2348-2356.

(25) Roper R L, Wolfe E J, Weisberg A, Moss B: The envelope protein encoded by the A33R gene is required for formation of actin-containing microvilli and efficient cell-to-cell spread of vaccinia virus. J Virol 1998; 72(5):4192-4204.

(26) Roper R L, Payne L G, Moss B: Extracellular vaccinia virus envelope glycoprotein encoded by the A33R gene. J Virol 1996; 70(6):3753-3762.

(27) Wolfe E J, Weisberg A S, Moss B: The vaccinia virus A33R protein provides a chaperone function for viral membrane localization and tyrosine phosphorylation of the A36R protein. J Virol 2001; 75(1):303-310.

(28) Duncan S A, Smith G L: Identification and characterization of an extracellular envelope glycoprotein affecting vaccinia virus egress. J Virol 1992; 66(3):1610-1621.

(29) Rottger S, Frischknecht F, Reckmann I, Smith G L, Way M: Interactions between vaccinia virus IEV membrane proteins and their roles in IEV assembly and actin tail formation. J Virol 1999; 73(4):2863-2875.

(30) Wolfe E J, Katz E, Weisberg A, Moss B: The A34R glycoprotein gene is required for induction of specialized actin-containing microvilli and efficient cell-to-cell transmission of vaccinia virus. J Virol 1997; 71(5):3904-3915.

(31) McIntosh A A, Smith G L: Vaccinia virus glycoprotein A34R is required for infectivity of extracellular enveloped virus. J Virol 1996; 70(1):272-281.

(32) Sanderson C M, Frischknecht F, Way M, Hollinshead M, Smith G L: Roles of vaccinia virus EEV-specific proteins in intracellular actin tail formation and low pH-induced cell-cell fusion. J Gen Virol 1998; 79 (Pt 6):1415-1425.

(33) Scaplehorn N, Holmstrom A, Moreau V, Frischknecht F, Reckmann I, Way M: Grb2 and Nck act cooperatively to promote actin-based motility of vaccinia virus. Curr Biol 2002; 12(9):740-745.

(34) van E H, Hollinshead M, Smith G L: The vaccinia virus A36R protein is a type Ib membrane protein present on intracellular but not extracellular enveloped virus particles. Virology 2000; 271(1):26-36.

(35) Ward B M, Moss B: Vaccinia virus A36R membrane protein provides a direct link between intracellular enveloped virions and the microtubule motor kinesin. J Virol 2004; 78(5):2486-2493.

(36) Wolfe E J, Weisberg A S, Moss B: Role for the vaccinia virus A36R outer envelope protein in the formation of virus-tipped actin-containing microvilli and cell-to-cell virus spread. Virology 1998; 244(1):20-26.

(37) van E H, Hollinshead M, Rodger G, Zhang W H, Smith G L: The vaccinia virus F12L protein is associated with intracellular enveloped virus particles and is required for their egress to the cell surface. J Gen Virol 2002; 83:195-207.

(38) Parkinson J E, Sanderson C M, Smith G L: The vaccinia virus A38L gene product is a 33-kDa integral membrane glycoprotein. Virology 1995; 214(1):177-188.

(39) Sanderson C M, Parkinson J E, Hollinshead M, Smith G L: Overexpression of the vaccinia virus A38L integral membrane protein promotes Ca2+ influx into infected cells. J Virol 1996; 70(2):905-914.

(40) Seki M, Oie M, Ichihashi Y, Shida H: Hemadsorption and fusion inhibition activities of hemagglutinin analyzed by vaccinia virus mutants. Virology 1990; 175(2):372-384.

(41) Shida H: Nucleotide sequence of the vaccinia virus hemagglutinin gene. Virology 1986; 150(2):451-462.

(42) Shida H, Dales S: Biogenesis of vaccinia: carbohydrate of the hemagglutinin molecules. Virology 1981; 111(1): 56-72.

(43) Payne L G, Norrby E: Presence of haemagglutinin in the envelope of extracellular vaccinia virus particles. J Gen Virol 1976; 32(1):63-72.

(44) Katz E, Wolfe E J, Moss B: The cytoplasmic and transmembrane domains of the vaccinia virus B5R protein target a chimeric human immunodeficiency virus type 1 glycoprotein to the outer envelope of nascent vaccinia virions. J Virol 1997; 71(4):3178-3187.

(45) Herrera E, Lorenzo M M, Blasco R, Isaacs S N: Functional analysis of vaccinia virus B5R protein: essential role in virus envelopment is independent of a large portion of the extracellular domain. J Virol 1998; 72(1):294-302.

(46) Ward B M, Moss B: Golgi network targeting and plasma membrane internalization signals in vaccinia virus B5R envelope protein. J Virol 2000; 74(8):3771-3780.

(47) Hsiao J C, Chung C S, Chang W: Vaccinia virus envelope D8L protein binds to cell surface chondroitin sulfate and mediates the adsorption of intracellular mature virions to cells. J Virol 1999; 73(10):8750-8761.

(48) Senkevich T G, Weisberg A S, Moss B: Vaccinia virus E1OR protein is associated with the membranes of intracellular mature virions and has a role in morphogenesis. Virology 2000; 278(1):244-252.

(49) Senkevich T G, White C L, Koonin E V, Moss B: A viral member of the ERV1/ALR protein family participates in a cytoplasmic pathway of disulfide bond formation. Proc Natl Acad Sci USA 2000; 97(22):12068-12073.

(50) Zhang W H, Wilcock D, Smith G L: Vaccinia virus F12L protein is required for actin tail formation, normal plaque size, and virulence. J Virol 2000; 74(24):11654-11662.

(51) Blasco R, Moss B: Extracellular vaccinia virus formation and cell-to-cell virus transmission are prevented by deletion of the gene encoding the 37,000-Dalton outer envelope protein. J Virol 1991; 65(11):5910-5920.

(52) Husain M, Moss B: Similarities in the induction of post-Golgi vesicles by the vaccinia virus F13L protein and phospholipase D. J Virol 2002; 76(15):7777-7789.

(53) Husain M, Weisberg A, Moss B: Topology of epitope-tagged F13L protein, a major membrane component of extracellular vaccinia virions. Virology 2003; 308(2):233-242.

(54) Roper R L, Moss B: Envelope formation is blocked by mutation of a sequence related to the HKD phospholipid metabolism motif in the vaccinia virus F13L protein. J Virol 1999; 73(2):1108-1117.

(55) Schmutz C, Rindisbacher L, Galmiche M C, Wittek R: Biochemical analysis of the major vaccinia virus envelope antigen. Virology 1995; 213(1):19-27.

(56) White C L, Senkevich T G, Moss B: Vaccinia virus G4L glutaredoxin is an essential intermediate of a cytoplasmic disulfide bond pathway required for virion assembly. J Virol 2002; 76(2):467-472.

(57) White C L, Weisberg A S, Moss B: A glutaredoxin, encoded by the G4L gene of vaccinia virus, is essential for virion morphogenesis. J Virol 2000; 74(19):9175-9183.

(58) Ojeda S, Domi A, Moss B: Vaccinia virus G9 protein is an essential component of the poxvirus entry-fusion complex. J Virol 2006; 80(19):9822-9830.

(59) Senkevich T G, Moss B: Vaccinia virus H2 protein is an essential component of a complex involved in virus entry and cell-cell fusion. J Virol 2005; 79(8):4744-4754.

(60) da Fonseca F G, Wolfe E J, Weisberg A, Moss B: Effects of deletion or stringent repression of the H3L envelope gene on vaccinia virus replication. J Virol 2000; 74(16): 7518-7528.

(61) da Fonseca F G, Wolfe E J, Weisberg A, Moss B: Characterization of the vaccinia virus H3L envelope protein: topology and posttranslational membrane insertion via the C-terminal hydrophobic tail. J Virol 2000; 74(16):7508-7517.

(62) Lin C L, Chung C S, Heine H G, Chang W: Vaccinia virus envelope H3L protein binds to cell surface heparan sulfate and is important for intracellular mature virion morphogenesis and virus infection in vitro and in vivo. J Virol 2000; 74(7):3353-3365.

(63) Knipe D M, Howley P M: Fields Virology. ed Fifth, Philadelphia, USA, Lippincott Williams & Wilkins, a Wolthers Kluwer business, 2007.

(64) Takahashi T, Oie M, Ichihashi Y: N-terminal amino acid sequences of vaccinia virus structural proteins. Virology 1994; 202(2):844-852.

(65) Law K M, Smith G L: A vaccinia serine protease inhibitor which prevents virus-induced cell fusion. J Gen Virol 1992; 73 (Pt 3):549-557.

(66) Turner P C, Moyer R W: An orthopoxvirus serpinlike gene controls the ability of infected cells to fuse. J Virol 1992; 66(4):2076-2085.

(67) Turner P C, Moyer R W: The cowpox virus fusion regulator proteins SPI-3 and hemagglutinin interact in infected and uninfected cells. Virology 2006; 347(1):88-99.

(68) Zhou J, Sun X Y, Fernando G J, Frazer I H: The vaccinia virus K2L gene encodes a serine protease inhibitor which inhibits cell-cell fusion. Virology 1992; 189(2):678-686.

(69) Su H P, Garman S C, Allison T J, Fogg C, Moss B, Garboczi D N: The 1.51-Angstrom structure of the poxvirus L1 protein, a target of potent neutralizing antibodies. Proc Natl Acad Sci USA 2005; 102(12):4240-4245.

(70) Townsley A C, Senkevich T G, Moss B: The product of the vaccinia virus L5R gene is a fourth membrane protein encoded by all poxviruses that is required for cell entry and cell-cell fusion. J Virol 2005; 79(17):10988-10998.

The invention claimed is:

1. A method for the aseptic purification of biologically active Vaccinia virus comprising:
   i) aseptically loading a solid-phase matrix having a pore size of greater than 0.25 μm, to which a ligand is attached, with a Vaccinia virus suspension, wherein the ligand is a glucosamine glycan (GAG) ligand;
   ii) aseptically washing the matrix; and
   iii) aseptically eluting the virus.

2. The method according to claim 1, wherein the Vaccinia virus is a recombinant Vaccinia virus.

3. The method according to claim 1, wherein the Vaccinia virus is MVA or recombinant MVA.

4. The method according to claim 1, wherein the solid-phase matrix comprises or is a membrane.

5. The method according to claim 4, wherein the solid-phase matrix comprises or is a cellulose membrane.

6. The method according to claim 1, wherein the ligand comprises a negatively charged sulfate group.

7. The method according to claim 1, wherein the ligand is heparan sulfate.

8. The method according to claim 1, wherein the ligand is heparin.

9. The method according to claim 1, wherein contaminants are removed from the Vaccinia virus in the liquid-phase culture.

10. The method according to claim 1, additionally comprising a purification step by ion-exchange.

11. The method of claim 1, further comprising administering the eluted Vaccinia virus to an animal.

12. The method according to claim 11, wherein the animal is a mammal.

13. The method of claim 12, wherein the mammal is a human.

14. A method for the aseptic purification of biologically active Vaccinia virus comprising:
   i) aseptically adjusting the pH of a Vaccinia virus suspension to 4.9-6.0;
   ii) aseptically loading a solid-phase matrix, to which a ligand is attached, with the adjusted Vaccinia virus suspension, wherein the ligand is a glucosamine glycan (GAG) ligand;
   iii) aseptically washing the matrix; and
   iv) aseptically eluting the virus.

15. A method for the aseptic purification of biologically active Vaccinia virus comprising:
   i) aseptically loading a solid-phase matrix, to which a ligand is attached, with a Vaccinia virus suspension, wherein the ligand is a glucosamine glycan (GAG) ligand;
   ii) aseptically washing the matrix; and
   iii) aseptically eluting the virus with sodium chloride (NaCl).

16. The method according to claim 15, wherein the Vaccinia virus is eluted by an increasing NaCl concentration gradient ranging from 0.15 M to 2.0 M.

* * * * *